US00PP19875P2

(12) United States Plant Patent
Austin

(10) Patent No.: US PP19,875 P2
(45) Date of Patent: Mar. 31, 2009

(54) ***ROSA HYBRIDA* SHRUB NAMED 'AUSLOFTY'**

(50) Latin Name: *Rosa hybrida*
Varietal Denomination: AUSlofty

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 12/001,101

(22) Filed: Dec. 10, 2007

(30) Foreign Application Priority Data

Oct. 16, 2007 (GB) ..... AFP5/2100

(51) Int. Cl.
*A01H 5/00* (2006.01)

(52) U.S. Cl. ..... Plt./106

(58) Field of Classification Search ..... Plt./105, Plt./106
See application file for complete search history.

*Primary Examiner*—Kent L Bell
(74) *Attorney, Agent, or Firm*—Kauth, Pomeroy, Peck & Bailey LLP

(57) ABSTRACT

A variety of rose plant of the shrub class, named 'AUSlofty' is disclosed. The 'AUSlofty' rose is a plant suitable for repeat flowering production having medium apricot blooms, a strong tea fragrance and a vigorous upright growth.

1 Drawing Sheet

Classification: The present invention relates to a new *Rosa hybrida* shrub.

Variety denomination:

The new plant has the varietal denomination 'AUSlofty'.

ORIGIN OF INVENTION

This invention relates to a new and distinct variety of shrub rose plant named 'AUSlofty', which was originated by crossing two unnamed, unpatented varieties of *Rosa hybrida.*

BACKGROUND OF THE INVENTION

The primary objective of this breeding was to produce a very healthy repeat flowering variety having apricot blooms with a strong fragrance and vigorous upright growth.

SUMMARY OF THE INVENTION

Among the features which distinguish the new variety from other presently available and commercial rose cultivars known to the inventor is the following combination of characteristics: apricot blooms with a strong fragrance and vigorous upright growth.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSlofty' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the parent has pink blooms, 'AUSlofty' bears flowers of apricot and a strong tea fragrance. The new variety is classified as a *hybrida* rose with a broad growing habit.

The new variety may be distinguished from its pollen parent, by the following combination of characteristics: whereas the pollen parent bears small yellow blooms, 'AUSlofty' bears medium size flowers of apricot.

COMPARISON WITH THE CLOSEST COMMERCIALLY AVAILABLE CULTIVAR

The closest commercially available cultivar to the new variety is the 'AUSwinter' (U.S. Plant Pat. No. 13,484). The new rose may be distinguished from the 'AUSwinter' variety by the following combination of characteristics: the 'AUSwinter' has more petals, and a stronger anthocyanin color on the new growth compared to 'AUSlofty'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of September. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 1.9 cm long and 1.5 cm in diameter when the petals start to unfurl. Form: The bud form is pointed ovoid. Color: When sepals first divide, the bud color is Orange Group 28A. When half blown, the upper sides of the petals are Orange Group 25B, and the lower sides of the petals are Yellow-Orange Group 21B. Calyx: Shape: funnel-shaped. Sepals: Arrangement: Regular. Color: Upper Surface: Greyed-Green Group 193B. Lower Surface: Yellow-Green Group 144A. Length: 2.5 cm. Width: 1 cm. Shape: Subulate. Surface texture: Upper Surface: Pubescent. Lower Surface: Smooth. Number: There are three lightly appendaged sepals. There are 3 unappendaged sepals. Apex: The typical and observe sepal apex has medium extensions. Margin: The typical and observe unappendaged sepals have glandular edges.

*Receptacles.*—Color: Yellow-Green Group 144A. Shape: Funnel. Size: small, about 0.8 cm×0.7 cm. Surface: Smooth.

*Peduncle.*—Length: medium, averaging about 6 cm. Diameter: The typical and observed diameter is about 3 mm. Surface: Smooth. Color: Yellow-Green Group 146A overlaid with strong concentration of Greyed-Purple Group 184A. Strength: Normal.

*Blooms.*—Size: Medium, average open diameter is about 9 cm. Borne: In clusters of 5–7 blooms having corymb shaped inflorescence. Stems: Strength: Normal, average length is about 75 cm. Diameter: 4 mm. Form: When first open, bloom is cupped. Permanence of bloom: Outer petals curl back.

*Petalage.*—Number of petals under normal conditions: 90. Color: The upper sides of the petals are Orange Group 24A. The reverse sides of the petals are Yellow-Orange Group 23D. The base of the petals is Yellow-Orange Group 22B. Discoloration: The general tonality at the end of the first day is: Orange Group 24A. At the end of the third day is: Yellow-Orange Group 22C. Fragrance: Strong. Character of fragrance: Tea.

*Petals.*—Texture: Smooth. Size: Width: 2.7 cm. Length: 4 cm. Surface: Smooth. Shape: Obovate. Margin: Notched, to varying degrees. Apex Shape: Emarginate. Base Shape: Obtuse. Form: Slightly incurved. Arrangement: Quartered. Petaloids: Number: None. Persistence: Petals hang on and dry. Lastingness: On the plant: fair, about 5–6 days. As a cut flower: about 3–4 days.

*Reproductive parts.*—Stamens: Number: 13. Length: 6.5 mm. Anthers: Length: 1.5 mm. Color: Yellow-Orange Group 17C. Arrangement: Regular around styles. Filaments: Color: Yellow Group 13B. Length: 10 mm. Pollen: Color: Yellow-Orange Group 17C. Pistils: Number: 20 –25. Length: 9.5–10 mm. Styles: Color: Green-Yellow Group 1C. Length: 9 mm. Stigmas: Color: Yellow-Orange Group 22A. Length: 0.5–1 mm. Hips: None Observed.

Plant characteristics:

*Plant form.*—Shrub.

*Plant growth.*—Vigorous and upright.

*Age to maturity.*—Two years.

Mature plant:—Height: 1.5 m. Width:1 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves is: 5 –7 [including terminal leaflet]. Size: Medium, about 15 cm long×9 cm wide. Quantity: Normal. Number of leaves per flowering stem is: 14. Color: New foliage: Upper side: Yellow-Green Group 146B, overlaid with Greyed-Red Group 181B. Lower side: Yellow-Green Group 146C. Old foliage: Upper side: Green Group N134A. Lower side: Green Group 137C. Leaflets Size: About 5 cm long×3 cm wide. Shape: Oval. Base Shape: Obtuse. Apex Shape: Acuminate. Texture: Wrinkled. Edge: Serrated. Serrations: Single. Petiote: Color: Green Group 137B with some patches of Greyed-Red Group 181A. Length: 3 cm. Width: 2 mm. Surface Texture: Prickly. Petiole Rachis: Color: Green Group 138A with some patched of Greyed-Red Group 181A. Underside: with prickles. Stipules: Length: 2.2 cm, glandular. Color: Yellow-Green Group 144B. Auricle: Shape: Awl-shaped. Length: 3 mm. Width: 1.5 mm at base tapering to point. Color: Yellow-Green Group 144B. Vein Color: Green Group 137C. Venation Pattern: Reticulate.

*Wood.*—New Wood: Color: Greyed-Purple Group 183A. Bark: Smooth. Old Wood: Color: Yellow-Green Group 146B. Bark: Smooth.

*Branching habit.*—Number: 8 per main stem. Lateral Branch Dimensions: Length: 30 cm. Diameter: 3 mm.

*Stems.*—Mature Stem: Length: 90 cm. Diameter: 4 mm. Internode Distance: 10 cm. The above measurements are all variable, depending on growing conditions in a season. Stem Pubescence Present: No. Color: Green Group 146B.

*Prickles.*—Quantity: On main canes from base: few. Number per stem length: 5 per 10 cm. On laterals from main canes: few. Number per stem length: 3 per 10 cm. Form: Hooked downward. Length: 10 mm. Color when young: Red-Purple Group 60A. Color when mature: Greyed-Orange Group 177A.

*Small prickles.*—Quantity: Main stalk: None. Laterals: None.

*Disease resistance.*—Mildew: Resistant to Powdery Mildew and Downy Mildew. Blackspot: Resistant. Rust: Resistant.

*Pest resistance.*—Not tested.

*Winter hardiness.*—Not tested.

*Growing conditions.*—Normal for a garden rose, namely, outdoors in soil.

What is claimed is:

1. A new and distinct variety of rose plant of the shrub class suitable for repeat flower production, substantially as herein shown and described.

* * * * *

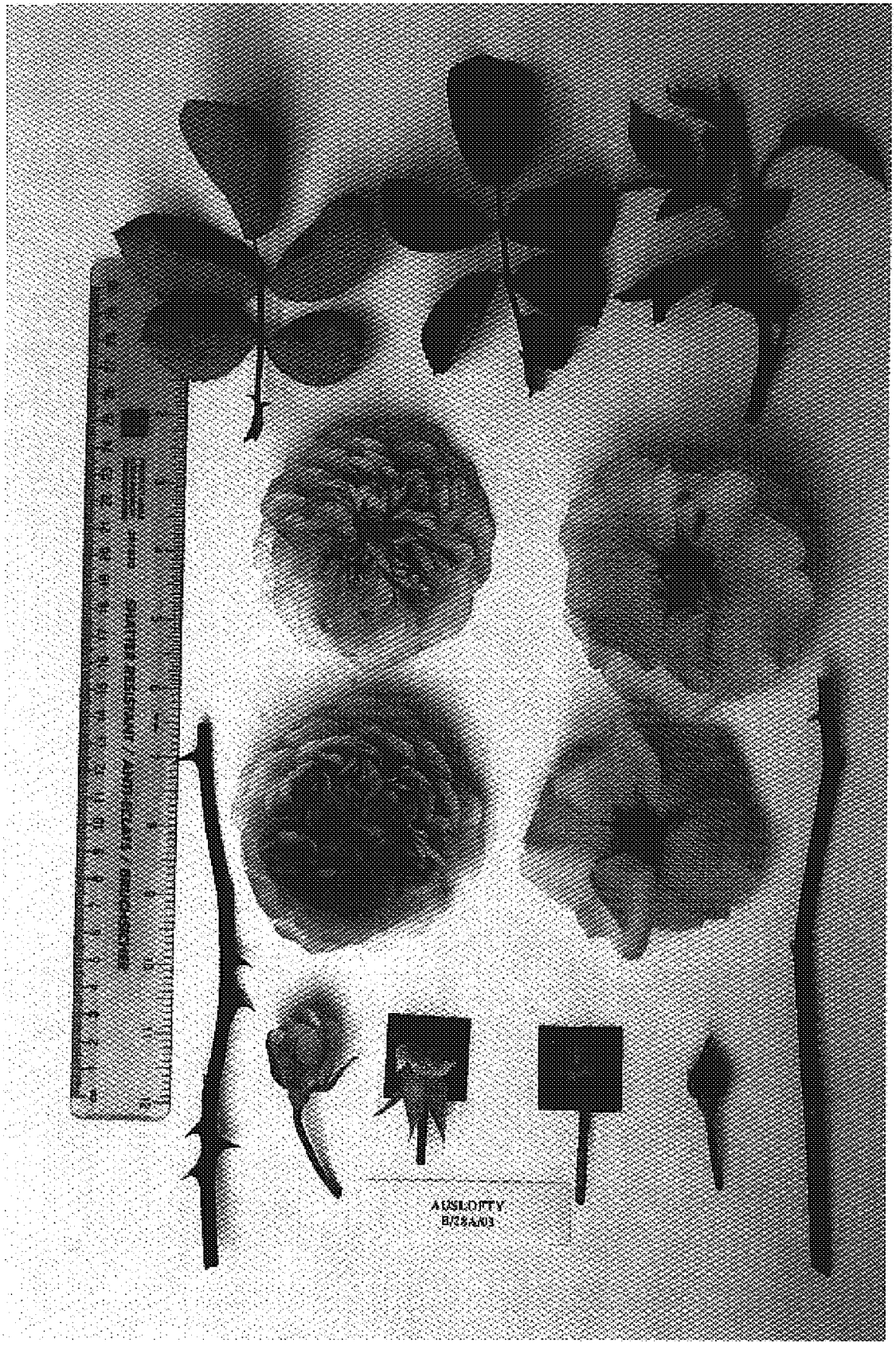
AUSLOFTY
8/28/03